US 9,757,029 B2

(12) United States Patent
Nozato et al.

(10) Patent No.: US 9,757,029 B2
(45) Date of Patent: Sep. 12, 2017

(54) FUNDUS IMAGING APPARATUS AND IMAGING METHOD

(71) Applicant: CANON KABUSHIKI KAISHA, Tokyo (JP)

(72) Inventors: Koji Nozato, Rochester, NY (US); Tomoyuki Makihira, Tokyo (JP); Kazuhide Miyata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 77 days.

(21) Appl. No.: 14/251,820

(22) Filed: Apr. 14, 2014

(65) Prior Publication Data

US 2014/0313479 A1    Oct. 23, 2014

(30) Foreign Application Priority Data

Apr. 17, 2013    (JP) .................. 2013-086790

(51) Int. Cl.
| | |
|---|---|
| *A61B 3/14* | (2006.01) |
| *A61B 3/113* | (2006.01) |
| *A61B 3/00* | (2006.01) |
| *A61B 3/12* | (2006.01) |
| *A61B 3/10* | (2006.01) |

(52) U.S. Cl.
CPC ............ *A61B 3/113* (2013.01); *A61B 3/0008* (2013.01); *A61B 3/1025* (2013.01); *A61B 3/12* (2013.01); *A61B 3/14* (2013.01)

(58) Field of Classification Search
CPC .. A61B 3/14; A61B 3/12; A61B 3/103; A61B 3/1015
USPC .................. 351/200, 205, 206, 246
See application file for complete search history.

(56) References Cited

U.S. PATENT DOCUMENTS

| | | | |
|---|---|---|---|
| 6,271,915 B1 * | 8/2001 | Frey et al. ................ 356/124 |
| 6,299,311 B1 * | 10/2001 | Williams et al. ............ 351/221 |
| 7,758,189 B2 | 7/2010 | Hammer et al. | |
| 8,204,300 B2 | 6/2012 | Sugita et al. | |
| 8,384,908 B2 | 2/2013 | Sugita et al. | |
| 8,390,818 B2 | 3/2013 | Hirose et al. | |

(Continued)

FOREIGN PATENT DOCUMENTS

| | | |
|---|---|---|
| EP | 2 420 181 A1 | 2/2012 |
| EP | 2 762 060 A2 | 8/2014 |

OTHER PUBLICATIONS

Nov. 6, 2014 Great Britain Official Action in Great Britain Patent Appln. No. 1406876.1.

(Continued)

*Primary Examiner* — James Greece
(74) *Attorney, Agent, or Firm* — Fitzpatrick, Cella, Harper & Scinto

(57) ABSTRACT

Provided is an imaging method for correcting aberration generated when imaging an object to be inspected. The imaging method includes: irradiating an imaging area with a first light beam which is scanned by a scan unit and taking an image of the object to be inspected based on return light of the first light beam; detecting a moving amount of the object to be inspected; comparing the detected moving amount with a predetermined threshold value; and adjusting the imaging area to be irradiated with the first light beam. The adjusting includes determining in accordance with a result of the comparison to change the imaging area by at least one of: using the scan unit, and using an aberration correcting unit.

18 Claims, 9 Drawing Sheets

(56) References Cited

U.S. PATENT DOCUMENTS

| | | |
|---|---|---|
| 8,605,768 B2 | 12/2013 | Furusawa et al. |
| 8,646,915 B2 | 2/2014 | Nozato |
| 2009/0285354 A1 | 11/2009 | Hirose et al. |
| 2011/0116042 A1 | 5/2011 | Nozato |
| 2011/0134394 A1 | 6/2011 | Srinivasan et al. |
| 2012/0002166 A1 | 1/2012 | Tomatsu et al. |
| 2012/0154746 A1 | 6/2012 | Nozato |
| 2012/0154747 A1 | 6/2012 | Makihira |
| 2012/0229761 A1 | 9/2012 | Makihira |
| 2012/0229762 A1 | 9/2012 | Makihira |
| 2012/0229763 A1 | 9/2012 | Suehira et al. |
| 2012/0229764 A1 | 9/2012 | Tomatsu et al. |
| 2012/0229765 A1 | 9/2012 | Makihira |
| 2012/0249956 A1* | 10/2012 | Narasimha-Iyer et al. .. 351/206 |
| 2012/0320338 A1 | 12/2012 | Hirose et al. |
| 2012/0327365 A1 | 12/2012 | Makihira |
| 2013/0070988 A1 | 3/2013 | Makihira |
| 2013/0182219 A1 | 7/2013 | Numajiri et al. |
| 2013/0201448 A1 | 8/2013 | Nozato |
| 2013/0215386 A1 | 8/2013 | Utagawa et al. |
| 2013/0215387 A1 | 8/2013 | Makihira et al. |
| 2013/0235342 A1 | 9/2013 | Makihira |
| 2013/0265546 A1 | 10/2013 | Nozato |
| 2014/0211157 A1 | 7/2014 | Nakahara et al. |
| 2014/0313479 A1 | 10/2014 | Nozato et al. |

OTHER PUBLICATIONS

Yan Zhang, et al., "High-speed volumetric imaging of cone photoreceptors with adaptive optics spectral-domain optical coherence tomography", Optics Express, vol. 14, No. 10, pp. 4380-4394, May 15, 2006.

May 3, 2016 German Official Action in German Patent Appln. No. 102014207328.6.

* cited by examiner

FUNDUS IMAGING APPARATUS AND IMAGING METHOD

BACKGROUND OF THE INVENTION

Field of the Invention

The present invention relates to a fundus imaging apparatus and method, and more particularly, to a fundus imaging apparatus and an imaging method for scanning a fundus with irradiation light to obtain a fundus image.

Description of the Related Art

In recent years, as a device for taking a fundus image, the use of a fundus imaging apparatus for scanning with irradiation light to take a fundus image, such as a confocal scanning laser ophthalmoscope (SLO) for acquiring a still or moving image of high resolution, has been popular. In such a fundus imaging apparatus, some time is required from the start to the end of the imaging. Therefore, the imaging is susceptible to involuntary eyeball movements called flicks, eyeball movements due to poor fixation, or the movement of the eye accompanying the movement of the face. This adds more importance to fundus tracking for tracking the movement of a fundus (U.S. Pat. No. 7,758,189).

In addition, in such an ophthalmologic imaging apparatus, higher resolution has been achieved by using a higher NA of an irradiating laser in recent years. However, when taking a fundus image, it is necessary to take the image through the optical system of the eye such as the cornea and crystalline lens. Along with achieving higher resolution, the influences of aberrations of the cornea and the crystalline lens on image quality of a taken image have become larger. Therefore, studies have been made on an AO-SLO (Adaptive Optics—Scanning Laser Ophthalmoscope) and an AO-OCT (Adaptive Optics—Optical Coherence Tomography), in which aberration of the eye is measured, and an adaptive optics (AO) as a compensation optical system for correcting the aberration is incorporated in the optical system. For instance, "Y. Zhang et al, Optics Express, Vol. 14, No. 10, May 15, 2006" describes an example of the AO-OCT. In the AO-SLO and the AO-OCT, a wavefront of the eye is usually measured by the Shack-Hartmann wavefront sensor method, and a variable shape mirror or a spatial phase modulator is driven so as to correct the measured wavefront. By taking the fundus image through the variable shape mirror, or the spatial phase modulator, the AO-SLO and the AO-OCT can take a high resolution image.

Along with an improvement of the imaging resolution of the imaging apparatus, it is necessary to also improve tracking accuracy for tracking a movement of the fundus to be imaged. However, because the movement of the eye is complicated, it is difficult to perform high accuracy tracking simply by using the related-art optical axis adjustment unit used in U.S. Pat. No. 7,758,189.

SUMMARY OF THE INVENTION

In view of the above-mentioned problem, it is an object of the present invention to realize high accuracy eyeball tracking in an imaging apparatus having a high imaging resolution, thereby taking a fundus image with high image quality.

In order to solve the above-mentioned problem, according to one embodiment of the present invention, there is provided an imaging apparatus, including: an imaging unit configured to irradiate an imaging area of an object to be inspected with a first light beam which is scanned by a scan unit and to take an image of the object to be inspected based on return light of the first light beam; an aberration measuring unit configured to measure aberration generated in the object to be inspected; an aberration correcting unit configured to correct the aberration in accordance with the measured aberration; a detection unit configured to detect a moving amount of the object to be inspected; a comparing unit configured to compare the detected moving amount with a predetermined threshold value; a determining unit configured to determine in accordance with a result of the determination by the determining unit to change the imaging area by at least one of: using the scan unit, and using the aberration correcting unit; and a control unit configured to change the imaging area.

Further, in order to solve the above-mentioned problem, according to one embodiment of the present invention, there is provided an imaging method for correcting aberration generated when imaging an object to be inspected. The method including: irradiating an imaging area with a first light beam which is scanned by a scan unit and taking an image of the object to be inspected based on return light of the first light beam; detecting a moving amount of the object to be inspected; comparing the detected moving amount with a predetermined threshold value; determining in accordance with the result of the comparison to change the imaging area by at least one of: using the scan unit, and using an aberration correcting unit; and changing the imaging area to be irradiated with the first light beam in accordance with a result of the determination.

According to one embodiment of the present invention, it is possible to take a fundus image having high resolution with little influence of eyeball movement.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

Embodiments of the present invention are described below. However, the present invention is not limited by structures of the following embodiments.

First Embodiment

Now, a first embodiment of the present invention is described.

In this embodiment, description is given of an example in which a first fundus imaging apparatus is used as a tracking apparatus while a second fundus imaging apparatus is used as an adaptive optics (AO)-SLO apparatus. A beam of the tracking apparatus and a beam of the AO-SLO apparatus enter a fundus simultaneously, and tracking data is used in the control of the AO-SLO apparatus to thereby acquire a stable and high-quality AO-SLO image.

(Overall Configuration of Apparatus)

Figure 1:
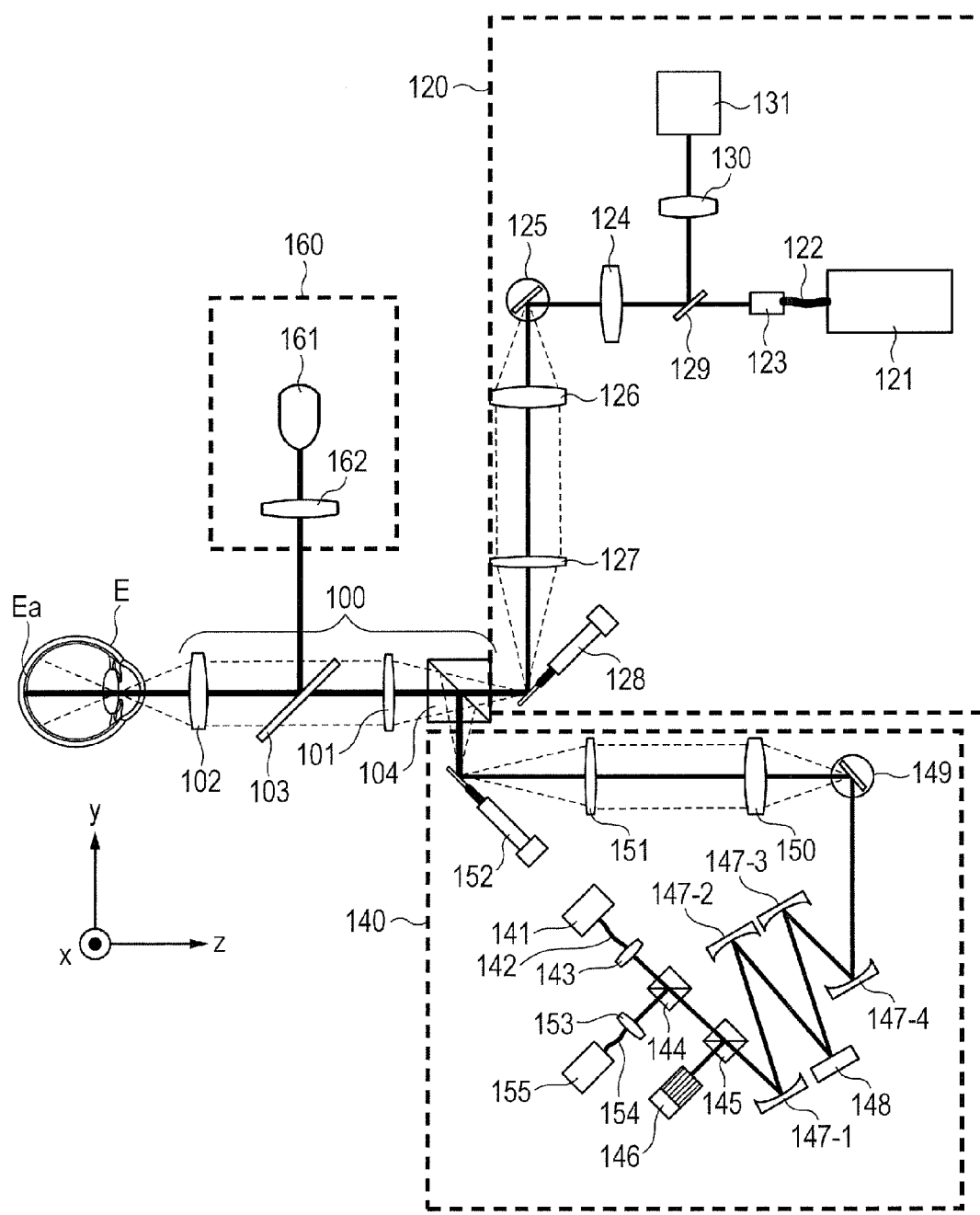
FIG. 1 is a schematic diagram of a structure of a fundus imaging apparatus in a first embodiment of the present invention.

The fundus imaging apparatus according to this embodiment is described with reference to the optical schematic diagram of FIG. 1.

The fundus imaging apparatus used in this embodiment includes the first fundus imaging apparatus, the second fundus imaging apparatus, and an internal fixation target apparatus.

The first fundus imaging apparatus includes an ocular lens unit 100 and an SLO 120. A laser light source 121 may suitably be a semiconductor laser or a super luminescent diode (SLD) light source. In order to reduce the brightness of a subject and maintain the resolution for fundus observation, the wavelength to be used is suitably a near infrared wavelength range of 700 nm to 1,000 nm. In this embodiment, a semiconductor laser having a wavelength of 780 nm is used. The light emitted from the laser light source 121 is transmitted through a fiber 122 to a fiber collimator 123, and is emitted from the fiber collimator 123 as a collimated light beam (measurement light).

The light beam is guided to an SLO scanner (X) 128 through a lens 124, an SLO scanner (Y) 125, and relay lenses 126 and 127. The light beam is further transmitted through a scan lens 101 and an ocular lens 102 to enter an eye to be inspected E. In this embodiment, galvano scanners are used as the SLO scanners (X) 128 and (Y) 125.

The z, x, and y coordinates to be used in this embodiment correspond to an eye axis direction, and correspond to a horizontal direction and a vertical direction with respect to a fundus image, respectively. In this embodiment, the x direction corresponds to a main scanning direction, and the y direction corresponds to a sub scanning direction.

The light beam that has entered the eye to be inspected E irradiates a fundus Ea of the eye to be inspected E as a spot beam. This spot beam is reflected or scattered by the fundus Ea of the eye to be inspected E and follows the same optical path to return to a ring mirror 129. Of the light that irradiates the fundus Ea and is reflected and scattered, the light that has passed through a portion around the pupil (reflected light) is reflected by the ring mirror 129 and received by an avalanche photodiode (hereinafter referred to as APD) 131 through a lens 130.

The second fundus imaging apparatus includes the ocular lens unit 100 having the same structure as that of the first fundus imaging apparatus described above and an AO-SLO unit 140 including an AO device. A light source 141 is an SLD light source having a wavelength of 840 nm. The light source 141 is shared by fundus imaging and wavefront measurement in this embodiment, but it is possible to adopt a structure in which separate light sources are arranged and light beams are combined in the middle of optical paths.

The light emitted from the light source 141 is transmitted through a fiber 142 to a fiber collimator 142, and is radiated from the fiber collimator 143 as collimated measurement light. The radiated measurement light is transmitted through a beam splitter 144 and guided to a compensation optical system.

The compensation optical system includes a beam splitter 145, a wavefront sensor 146 for measuring aberration, a wavefront correction device 148, and reflection mirrors 147-1 to 147-4 for guiding the light to those components. The reflection mirrors 147-1 to 147-4 are arranged so that at least the pupil of the eye to be inspected E, and each of the wavefront sensor 146 and the wavefront correction device 148, have an optically conjugate relationship. Further, in this embodiment, a spatial phase modulator using a liquid crystal element is used as the wavefront correction device 148.

The measurement light enters the wavefront correction device 148 to be reflected thereby, and is emitted to the reflection mirror 147-3. Similarly, the light that has returned from the fundus Ea of the eye to be inspected E also enters the wavefront correction device 148, and is then emitted to the reflection mirror 147-2. Further, the measurement light is scanned two-dimensionally by an AO-SLO scanner (X) 149 and an AO-SLO scanner (Y) 152. In this embodiment, a high-speed resonance scanner (scanner for main scanning) is used as the AO-SLO scanner (X) 149, and a galvano scanner (scanner for sub scanning) is used as the AO-SLO scanner (Y) 152.

The measurement light scanned by the AO-SLO scanners (X) 149 and (Y) 152 is reflected by a beam splitter 104 and transmitted through the scan lens 101 and the ocular lens 102 to enter the eye to be inspected E. The measurement light that has entered the eye to be inspected E is reflected or scattered by the fundus Ea and follows the same optical path back to the beam splitter 145. The beam splitter 145 allows a part of the measurement light to enter the wavefront sensor 146. The wavefront sensor 146 measures a wavefront of the measurement light, and a Shack-Hartmann sensor is used as the wavefront sensor 146. A part of the reflected/scattered light that has been transmitted through the beam splitter 145 is then reflected by the beam splitter 144 and guided to a light intensity sensor 155, including a photomultiplier tube (PM), through a fiber collimator 153 and a fiber 154.

The guided light reaching the light intensity sensor 155 is converted into an electric signal by the light intensity sensor 155 and subjected to imaging processing by a control portion (not shown). Then, when the control portion rotates the resonance scanner (the AO-SLO scanner (X) 149) and the galvano scanner (the AO-SLO scanner (Y) 152) by a minute angle, light intensity information from an imaging area of the fundus Ea is acquired, and an image is constructed as the fundus image to be displayed on a display apparatus (see FIG. 2) under the control of the control portion. Note that, the "minute angle" means an angle smaller than a scan angle of the SLO 120.

Further, the wavefront sensor 146 and the wavefront correction device 148 are connected to the control portion. The control portion calculates, based on the wavefront measured by the wavefront sensor 146, a modulation amount (correction amount) to correct the wavefront to a wavefront without aberration, and instructs the wavefront correction device 148 to perform the modulation. The measurement of the wavefront and instruction to the wavefront correction device 148 are repeatedly processed, with the result that feedback control is performed so that an optimal wavefront is always obtained. As a result, the aberration generated in the eye to be inspected is removed or reduced. In this embodiment, a reflective liquid crystal spatial phase modulator of 600×600 pixels is used as the wavefront correction device 148. As another example of the wavefront correction device 148, there is known a variable shape mirror including a film mirror and a plurality of actuators for driving the mirror. Both the liquid crystal spatial phase modulator in this embodiment, and the variable shape mirror, can change a direction of light locally on a reflection surface or in a transmitting portion so that the wavefront of transmitted light or reflected light can be changed.

An internal fixation target 160 includes a light source 161 and a lens 162. As the light source 161, a plurality of light emitting diodes (LD) arranged in a matrix are used. A turn-on position of the light emitting diodes is changed under the control of the control portion in accordance with the part desired to be imaged. Light from the light source 161 is guided to the eye to be inspected E by a dichroic mirror 103 via the lens 162. The light emitted from the light source 161 is 520 nm, and a desired pattern is displayed by the control portion.

(Functional Configuration)

Figure 2:
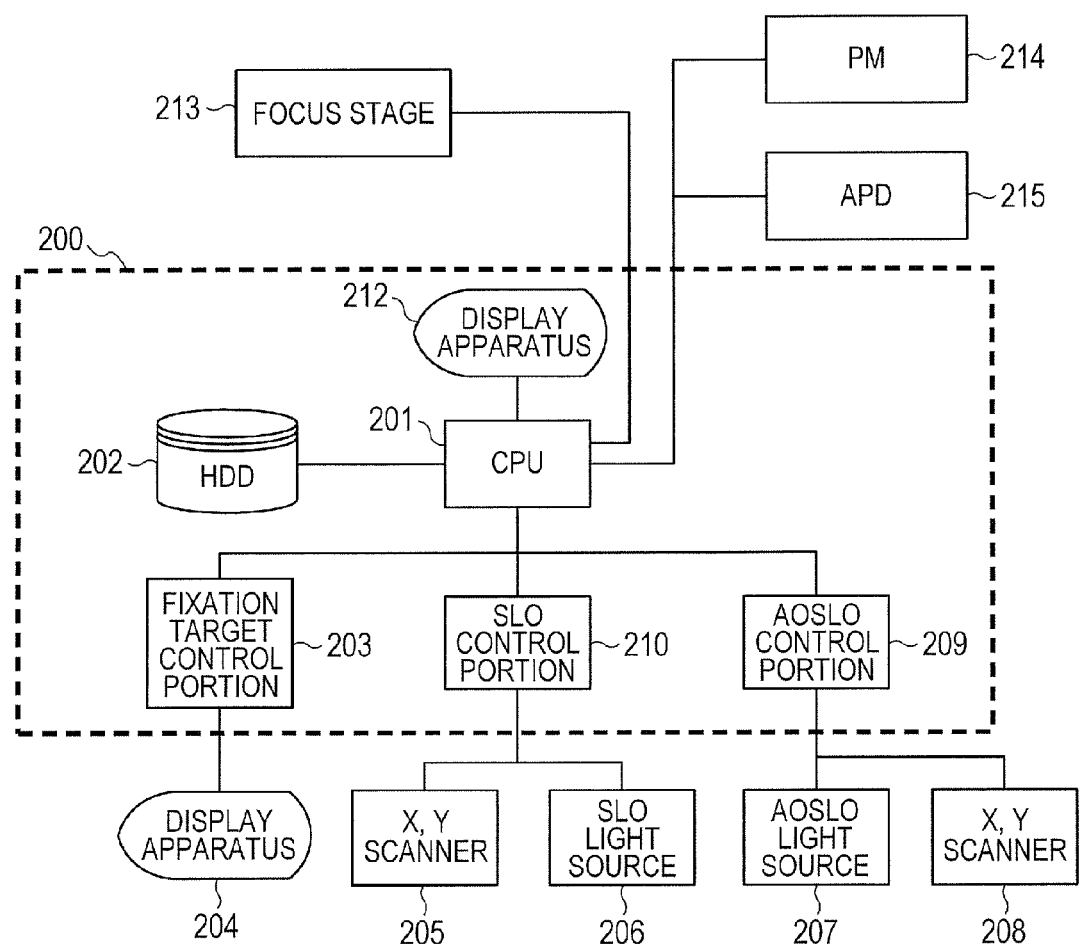
FIG. 2 is a functional schematic diagram of the fundus imaging apparatus in the first embodiment.

A functional configuration according to this embodiment is described with reference to FIG. 2. A control portion (PC) 200 for controlling functional members includes a display apparatus 212, a CPU 201, a storage device HDD 202, a fixation target control portion 203, an SLO control portion 210, and an AO-SLO control portion 209, which are control portions for the respective apparatus. Under instructions from the CPU 201, a display apparatus 204 (corresponding to the light source 161 of FIG. 1) for displaying the fixation target, an X-Y scanner 205 (corresponding to the SLO scanners 125 and 128 of FIG. 1), an SLO light source 206 (corresponding to the laser light source 121 of FIG. 1) of the SLO apparatus, an X-Y scanner 208 (corresponding to the AO-SLO scanners 149 and 152 of FIG. 1), and an AO-SLO light source 207 (corresponding to the light source 141 of FIG. 1) of the AO-SLO apparatus are operated under the control of the fixation target control portion 203, the SLO control portion 210, and the AO-SLO control portion 209, respectively. The wavefront sensor 146 and the wavefront correction device 148, which are components of the compensation optical system, are also controlled by the AO-SLO control portion 209.

Further, a signal from the eye to be inspected E is acquired via a PM 214 (corresponding to the light intensity sensor 155 of FIG. 1), which is a light receiving member of the AO-SLO apparatus, and an APD 215 (corresponding to the APD 131 of FIG. 1), which is a light receiving member of the SLO apparatus. The acquired signal is converted into an image by the CPU 201 and displayed on the display apparatus 212.

(Flow)

Figure 3:
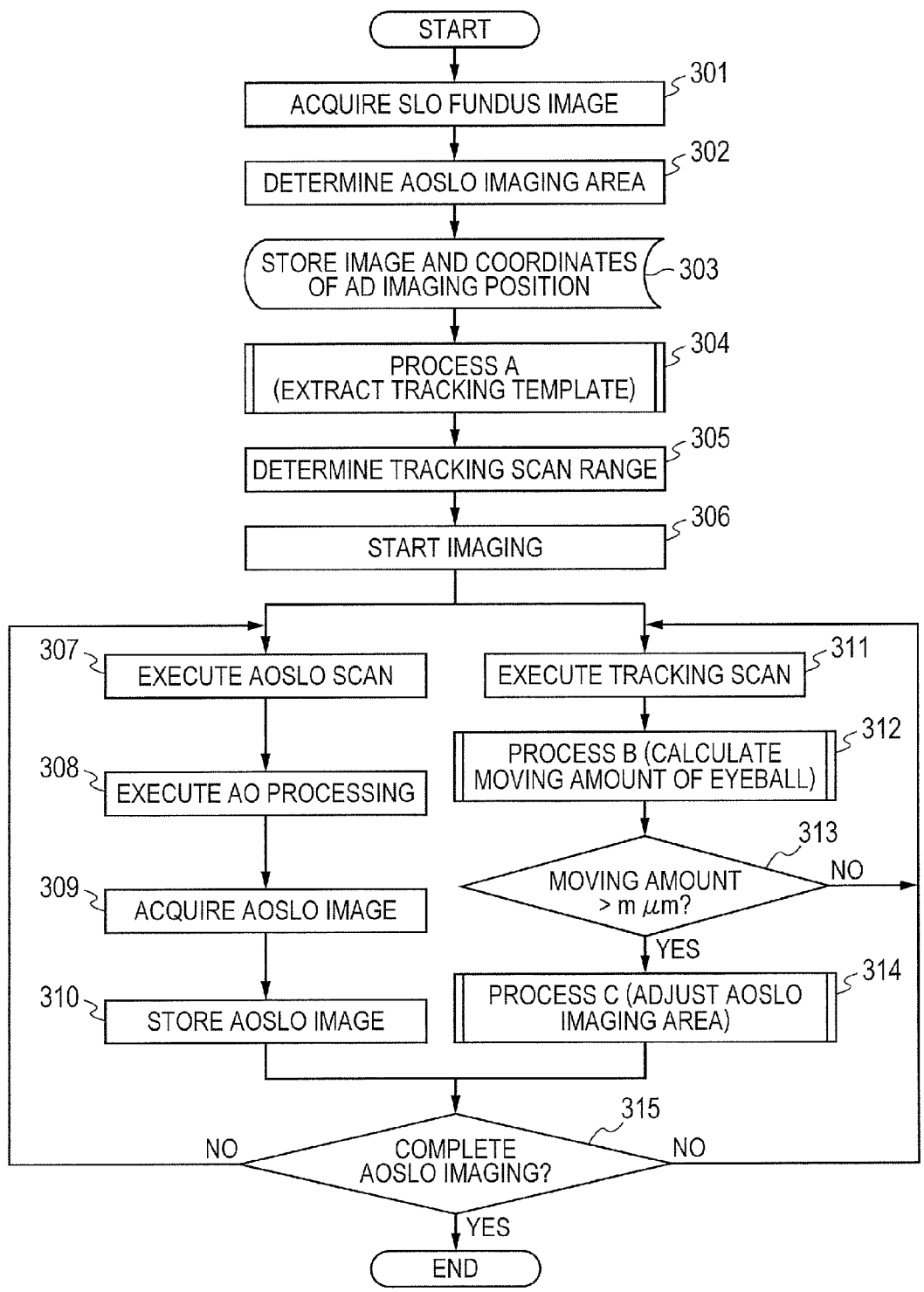
FIG. 3 is a procedure flow schematic diagram in the first embodiment.

With the above-mentioned apparatus, the SLO apparatus as the first fundus imaging apparatus is used for tracking, and the tracking result is fed back to the scanners of the AO-SLO apparatus and the wavefront correction device, to thereby acquire the AO-SLO image of a desired position stably. A flow thereof is illustrated in FIG. 3. Note that, unless otherwise noted, the processing is executed by the CPU 201.

First, the first fundus imaging apparatus acquires an SLO fundus image by outputting light from the laser light source 121, and receives the reflected light by the APD 131 in a state in which the fixation target 161 is turned on to be presented to the eye to be inspected E (Step 301). The first fundus imaging apparatus functions as a unit for taking a fundus image of the entire fundus of the eye to be inspected.

Based on an instruction by an operator from an input device (not shown), an AO-SLO imaging area is determined in the SLO image (Step 302). This processing is executed by a module area of the CPU 201 that functions as a first area setting unit for setting a first area of the eye to be inspected, which is irradiated with AO-SLO light as a first beam. The first area is set based on the fundus image acquired in advance. The set area to be imaged with the AO-SLO light is stored in a memory of the CPU 201 (Step 303).

From the taken fundus image, at least one template for tracking is extracted (Process A: Step 304). Specifically, based on the first area set by the first area setting unit, a second area of the eye to be inspected, which is to be irradiated with SLO light for tracking as a second beam, is set and extracted as the template. The setting of the second area is executed by a module area of the CPU 201 that functions as a second area setting unit. A certain area around the extracted template is determined as a tracking scan range (Step 305).

Imaging for a fundus image is started (Step 306), and the AO-SLO apparatus and the SLO apparatus are operated. The AO-SLO apparatus drives the X-Y scanner 208 to scan the imaging area determined in Step 302 (Step 307), and an AO-SLO signal is acquired and converted into an image (Step 309). Specifically, based on return light of the AO-SLO light as the first beam, an AO-SLO image as a first image of the eye to be inspected is generated. The image generation is executed by a module area of the CPU 201 that functions as a first generation unit. Thereafter, the AO-SLO image is stored in the HDD 202 (Step 310).

In this embodiment, an aberration correction process is executed in Step 308. In the aberration correction process, aberration is measured based on a signal from the wavefront sensor, and the wavefront correction device is driven in accordance with a result of the aberration measurement so as to correct the aberration.

In this embodiment, the measured wavefront is modeled to be a Zernike function, and coefficients of the orders are calculated. Then, a modulation amount of the wavefront correction device 148 is calculated based on the coefficients. In the calculation of the modulation amount, based on a reference modulation amount for forming shapes of Zernike orders by the wavefront correction device 148, the reference modulation amount is multiplied to all the coefficients of the measured Zernike orders, and further the results are all integrated to obtain a final modulation amount. In general, when constructing an eye correction optical system, a range approximately from the first to sixth orders of the Zernike function of the measured wavefront is used for modeling. For instance, the first order of the Zernike indicates horizontal and vertical propagation directions, and the second order indicates focus or astigmatism.

In Step 308, the process described above is repeated to a certain extent and is continued until an aberration amount is decreased to be an arbitrary threshold value or lower. In addition, the aberration correction process may be executed without synchronizing with imaging.

Simultaneously, using the X-Y scanner 205 of the SLO apparatus, the range determined in Step 305 is scanned (Step 311) to acquire an SLO image. In other words, a second image of the eye to be inspected for tracking is generated based on return light from the eye to be inspected of the second beam described above. The image generation is executed by a module area of the CPU 201 that functions as a second generation unit.

In the acquired SLO image, template matching is executed. By comparing coordinates of the template with matched coordinates, a movement of the eyeball (moving amount and direction) is calculated (Process B: Step 312). This calculation process is executed by a module area of the CPU 201 that functions as a detection unit for detecting the movement of the eye to be inspected based on the second image. Note that, the detection unit compares the image of the region extracted as the template with the second image that is newly generated and acquired at this stage so as to detect the movement, and also includes a unit for detecting the movement of the eye to be inspected by the comparison.

Next, the detected moving amount as the moving amount of the eye to be inspected, and a prescribed value (m) μm of the moving amount, are compared (Step 313). The prescribed value (m) corresponds to a predetermined threshold value that is compared with the moving amount in the comparing step of Step 313. The comparing step is executed by a module area of the CPU 201 that functions as a comparing unit. Here, when the moving amount does not exceed the prescribed value (m), the process proceeds to Step 315. When the moving amount exceeds the prescribed value (m), the moving amount is used to control correction of the imaging area of the AO-SLO apparatus (Yes in Step 313). The correction of the imaging area is executed based on the detected movement of the eye to be inspected, and this process is executed by a module area of the CPU 201 that functions as a correcting unit for correcting the first area. In other words, the prescribed value (m) described here is set as a reference value for determining whether or not it is necessary to adjust the imaging area by tracking the movement of the eyeball. In addition, the prescribed value (m) has a predetermined standard value but may be set in accordance with the eye to be inspected. For example, the prescribed value (m) may be set for each eye to be inspected or may be read from data stored in the storage device HDD 202.

The correction of the imaging area executed in Step 314 (Process C), namely the adjustment of the imaging area, is executed by correction of a scan range of a scanner as a scanning unit and a tilt correction by an aberration correction device. Note that, the correction of the scan range as a light beam irradiation range is appropriately executed by changing a light beam irradiation direction in this embodiment, but the present invention is not limited to this changing method.

When the AO-SLO imaging is complete, the processing is ended (Yes in Step 315).

Figure 4A:
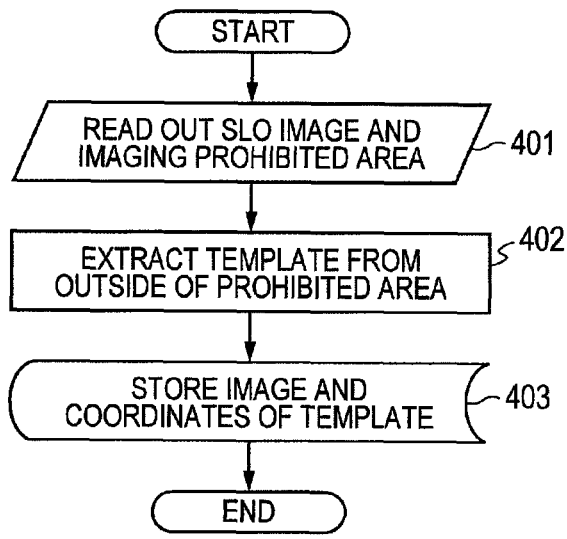
FIGS. 4A, 4B and 4C are detailed procedure flow schematic diagrams in the first embodiment.

Process A of Step 304 is described with reference to FIG. 4A. The SLO image and the prohibited area of the SLO imaging are read out (Step 401). The template is extracted from the SLO image outside the prohibited area (Step 402). The template coordinates and image are stored in the memory (Step 403).

Figure 4B:
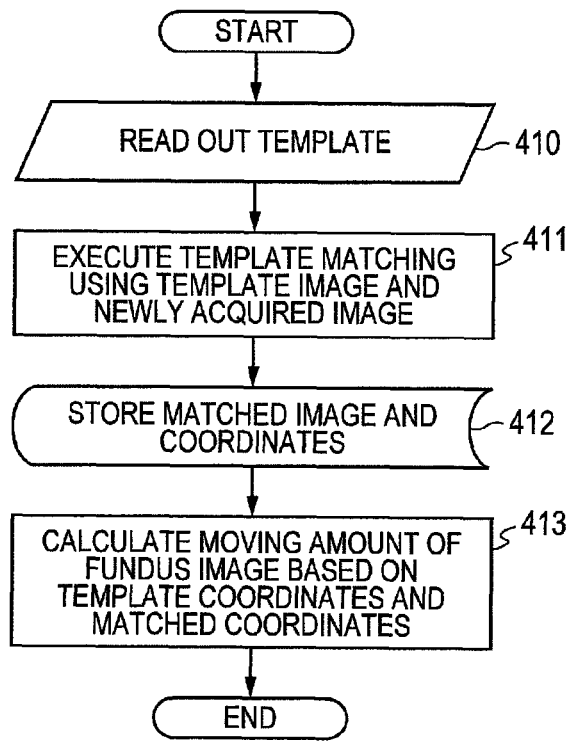

Process B is described with reference to FIG. 4B. The template image and coordinates are read out from the memory (Step 410). The read template image and a newly acquired SLO image are used to execute the template matching (Step 411). A matched image and coordinates are stored in the memory (Step 412). The movement of the fundus (moving amount and direction) is calculated based on the template coordinates and the matched coordinates (Step 413).

Figure 4C:
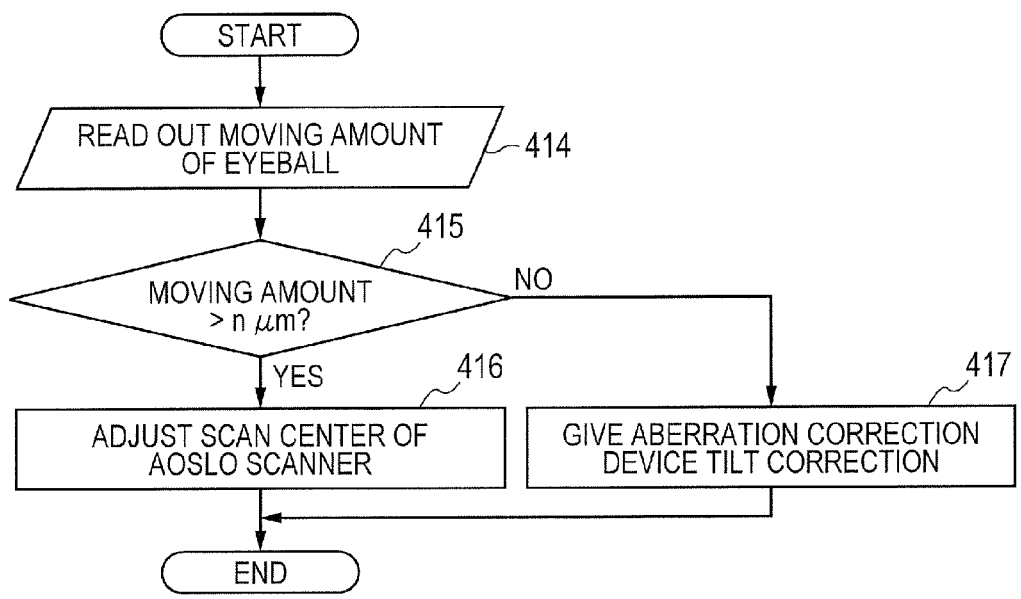

Process C is described with reference to FIG. 4C. The moving amount of the eyeball calculated in Step 312 is read out (Step 414). In this example, when the moving amount of the fundus is within a predetermined range, the aberration correction device adjusts an imaging position. When the moving amount of the fundus exceeds the predetermined range, the scan range of the beam scanning unit is adjusted. More specifically, it is determined in Step 415 whether or not the moving amount of the eyeball exceeds a given threshold value (n) μm. When the moving amount exceeds (n) μm, the process proceeds to Step 416, and a scan center of the scanner is adjusted based on the moving amount of the eye to be inspected, so as to adjust the beam irradiation range. The operation in Step 415 is also regarded as one form of the comparing step in the present invention. When the moving amount of the eyeball does not exceed the threshold value (n), tilt is instructed to the aberration correction device in Step 417. In other words, the threshold value (n) described here is set as a reference value for determining which one is more appropriate for the tracking operation of the eye to be inspected, operating the galvano scanner or the like to change the imaging area for performing tracking or giving a tilt by the aberration correction device for performing tracking. Further, the threshold value (n) corresponds to one form of the predetermined threshold value in the comparing step. Here, in a case where the tilt is instructed to the aberration correction device, the aberration correction device may be controlled to be driven promptly, or the correction device may be controlled to be driven after Zernike first order aberration, corresponding to the moving amount of the eyeball, is added to the wavefront measured by the wavefront sensor in the AO process in Step 308. Step 415 described above corresponds to a determination step of determining to perform at least which one of changing of the irradiation range by changing the beam irradiation direction, and changing of the beam irradiation range by the aberration correcting unit, in accordance with a result of the comparison in Step 313, and is executed by a module area of the CPU 201 that functions as a determining unit. In addition, Step 416 and Step 417 correspond to an adjusting step of adjusting the beam irradiation range, and are executed by a module area of the CPU 201 that functions as an adjustment unit. After the above-mentioned process is executed for the movement of the eye, control is made to scan the imaging area in Step 418.

Figure 6:
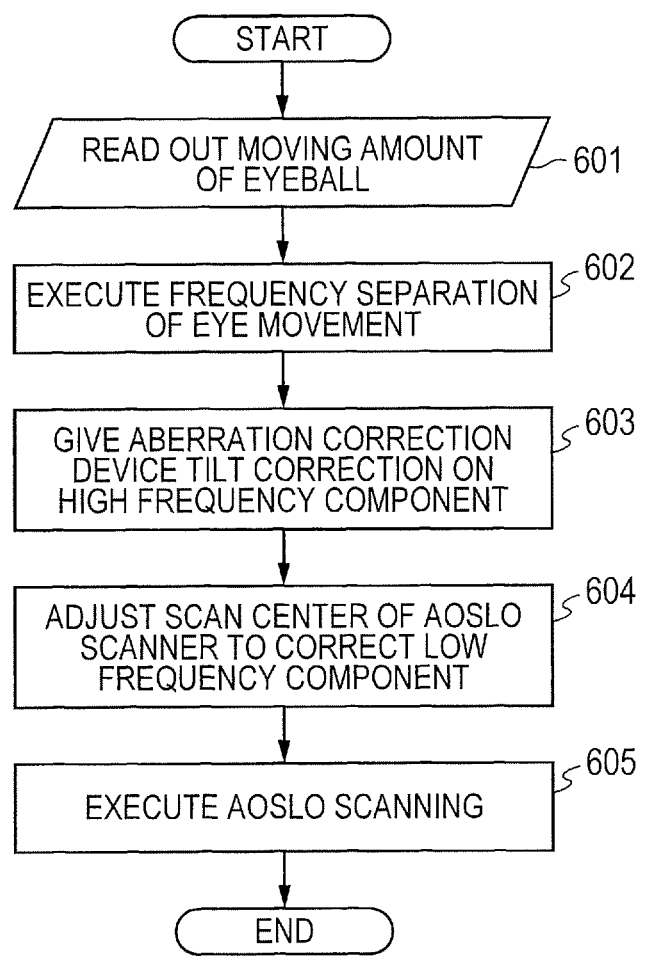
FIG. 6 is a detailed procedure flow schematic diagram in the first embodiment.

In addition, another example of Process C is described with reference to FIG. 6. A history of the moving amount of the eyeball calculated in Step 312 is stored, and the history is read out in Step 601. Frequency separation of the eye movement is executed based on the history of the read moving amount (Step 602). More specifically, detected position information is subjected to frequency separation such as Fourier transform so that high frequency components and low frequency components are separated and acquired from the components of the eye movement. Note that, in this separation, components having frequency values higher than a specific threshold value are regarded as the high frequency components, and components having frequency values lower than the specific threshold value are regarded as the low frequency component. However, it is preferred that this threshold value be changed in accordance with a structure of the apparatus, a subject, and the like. In this embodiment, the specific threshold value is 10 Hz as an initial value. In general, the movement of the eye is mostly occupied by a so-called drift having a low frequency and a large movement or amplitude, a so-called tremor having a high frequency and a small amplitude, and by a so-called saccade having a large emergent movement. Therefore, a micro high frequency movement and a large low frequency movement are separated by the above-mentioned method and are respectively corrected by different devices. In Step 603, the tilt instruction is given to the aberration correction device so as to correct the high frequency components. Also in this embodiment, the correction may be promptly executed, or may be executed at timing of the AO control. In addition, because the aberration correction device cannot correct a large movement in general, there may be employed a method involving further determining the moving amount and instructing the aberration correction device to execute the correction in a limited possible range while correcting the remaining portion by controlling another device. In Step 604, a center position of the scanning by the scanner is set so as to correct the low frequency components.

Figure 5:
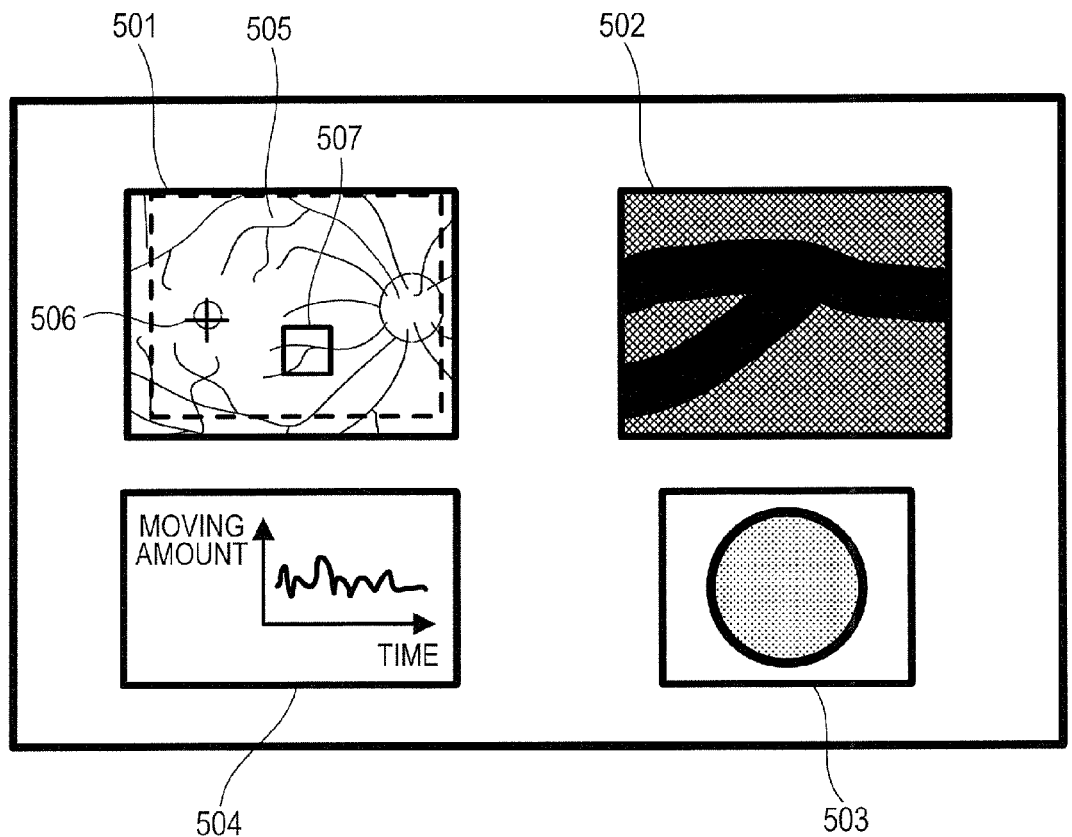
FIG. 5 is a GUI schematic diagram in the first embodiment.

In this way, while the AO-SLO imaging is performed, the tracking is performed so that an image of a desired position may be acquired. This enables photoreceptor analysis by superimposition of images, and bloodstream analysis by monitoring blood vessels. During imaging, images as illustrated in FIG. 5 are displayed on the display apparatus 212. A most recent tracking image 505, a most recent image 507 taken by the AO-SLO apparatus, and a fixation target position 506 are displayed on an initially-acquired SLO image 501 in the same screen, and a graph 504 of the moving amount of the eyeball, wavefront sensor information 503, and an AO-SLO image 502 are displayed on the display apparatus. In this embodiment, as a method of displaying the most recent information, the initially-acquired SLO image 501 with a wide angle of view and the fixation target position 506 are displayed while being moved along with the movement of the eyeball. As the display method, there may be employed a display method involving moving the most recent tracking image 505 and the AO-SLO image on the SLO image 501 having a wide angle of view.

An involuntary eyeball movement of the eye to be inspected is a combination of components of the tremor, the drift, and the saccade. Therefore, if an attempt is made to correct the image affected by the involuntary eyeball movement by a galvano scanner as a single optical axis adjustment unit as in the related art, there is a difficulty in tracking accuracy. In contrast, for example, it is conceivable to enhance the tracking accuracy by another optical axis adjustment unit. However, a resonant scanner, for example, cannot be used for tracking because it is difficult to control at a fixed position. In contrast, the aberration correction device inherently corrects a tilt component and has also an optical axis adjustment function so as to be capable of fine optical axis adjustment. In the present invention, this aberration correction device performs tracking in a direction in which the scanning is hitherto executed by using the resonant scanner, thereby enhancing tracking accuracy in a plurality of directions.

As described above, it is possible to perform high accuracy tracking in a high resolution AO-SLO by using a plurality of devices for imaging position adjustment, and it is possible to acquire an AO-SLO image with high image quality. In other words, according to the present invention, the aberration correction device as the wavefront correction device of the compensation optical system is used also in the imaging position adjustment unit, and hence high accuracy eyeball tracking can be realized, and a fundus image with high image quality can be acquired.

Second Embodiment

Now, a second embodiment of the present invention is described.

In this embodiment, description is given of an example in which a fundus position is calculated from an AO-SLO image, and fundus position data is reflected on AO-SLO imaging area control, to acquire a stable AO-SLO image with high image quality.

(Overall Configuration of Apparatus)

Figure 7:
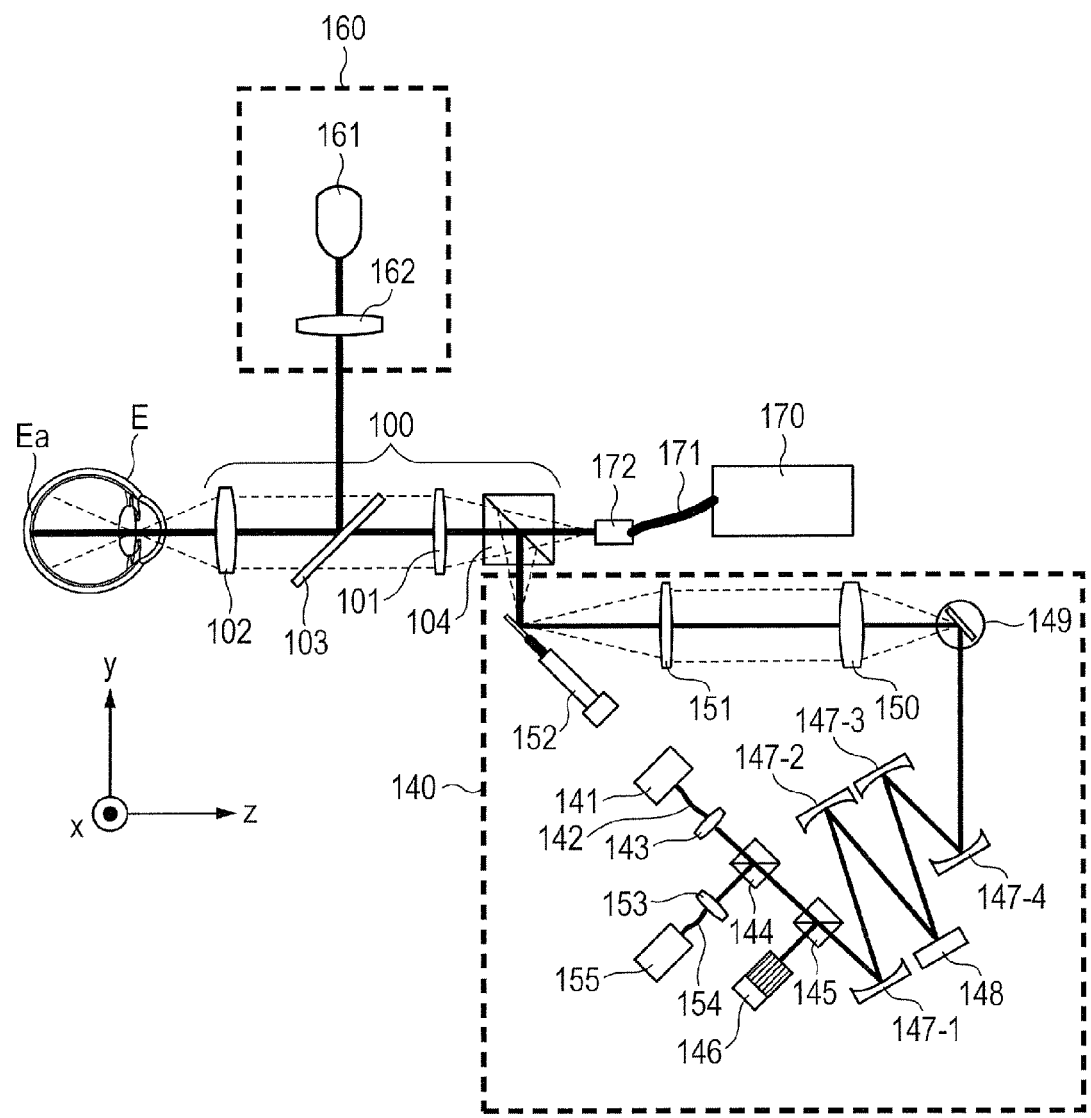
FIG. 7 is a schematic diagram of a structure of a fundus imaging apparatus in a second embodiment of the present invention.

The fundus imaging apparatus according to this embodiment is described with reference to an optical schematic diagram of FIG. 7.

The AO-SLO apparatus and the internal fixation target apparatus are similar to those in the first embodiment, and hence description thereof is omitted.

However, in this embodiment, wavefront measurement light for aberration correction enters the eye E. A laser light source 170 may suitably be a semiconductor laser or a super luminescent diode (SLD) light source. The wavelength to be suitably used is in a near infrared wavelength range of 700 nm to 1,000 nm, which is as close as possible to that used in the AO-SLO. In this embodiment, an SLD having a wavelength of 760 nm is used. The light emitted from the laser light source 170 is transmitted through a fiber 171 to a fiber collimator 172, and is emitted from a fiber collimator 172 as a collimated light beam (measurement light). The collimated light beam is transmitted through the beam splitter 104, the scan lens 101, and the ocular lens 102 to enter the eye to be inspected E, similarly to the AO-SLO measurement light. For instance, the beam splitter 104 is configured to transmit 50% of the wavefront measurement light and to reflect 100% of the AO-SLO measurement light. Then, it is possible to receive AO-SLO signal light at a minimum loss.

The beam splitter 145 just before the Shack-Hartmann sensor 146 as the wavefront sensor reflects 100% of the wavefront measurement light and transmits 100% of the AO-SLO measurement light. Then, it is possible to perform both the wavefront measurement and the fundus imaging at high efficiency.

The wavefront measurement light reflected and scattered by the fundus Ea reaches the beam splitter 145 in the same path as the AO-SLO and enters the wavefront sensor 146. The wavefront sensor 146 measures aberration from the incident wavefront measurement light and performs AO control based on the aberration.

(Functional Configuration)

Figure 8:
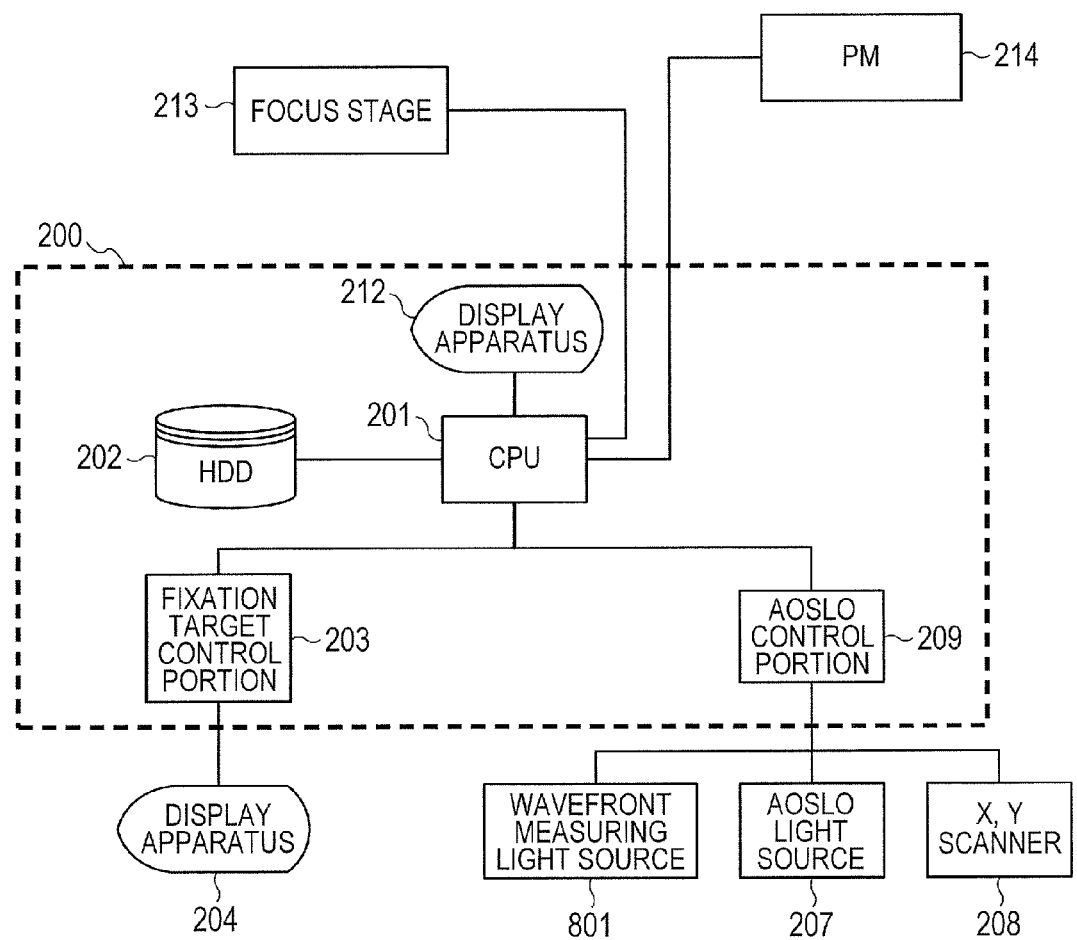
FIG. 8 is a functional schematic diagram of the fundus imaging apparatus in the second embodiment.

A functional configuration according to this embodiment is described with reference to FIG. 8. A control portion (PC) 200 for controlling functional members includes a display apparatus 212, a CPU 201, a storage device HDD 202, and a fixation target control portion 203 and an AO-SLO control portion 209, which are control portions for the respective apparatus. Under instructions from the CPU 201, a display apparatus 204 (corresponding to the light source 161 of FIG. 7) for displaying the fixation target, an X-Y scanner 208 (corresponding to the AO-SLO scanners 149 and 152 of FIG. 7), an AO-SLO light source 207 (corresponding to the light source 141 of FIG. 7) of the AO-SLO apparatus, and a wavefront measuring light source (corresponding to the light source 170 of FIG. 7) are operated under the control of the fixation target control portion 203 and the AO-SLO control portion 209, respectively. The wavefront sensor 146 and the wavefront correction device 148, which are components of the compensation optical system, are also controlled by the AO-SLO control portion 209.

Further, a signal from the eye to be inspected E is acquired via a PM 214 (corresponding to the light intensity sensor 155 of FIG. 7), which is a light receiving member of the AO-SLO apparatus. The acquired signal is converted into an image by the CPU 201 and displayed on the display apparatus 212.

(Flow)

Figure 9:
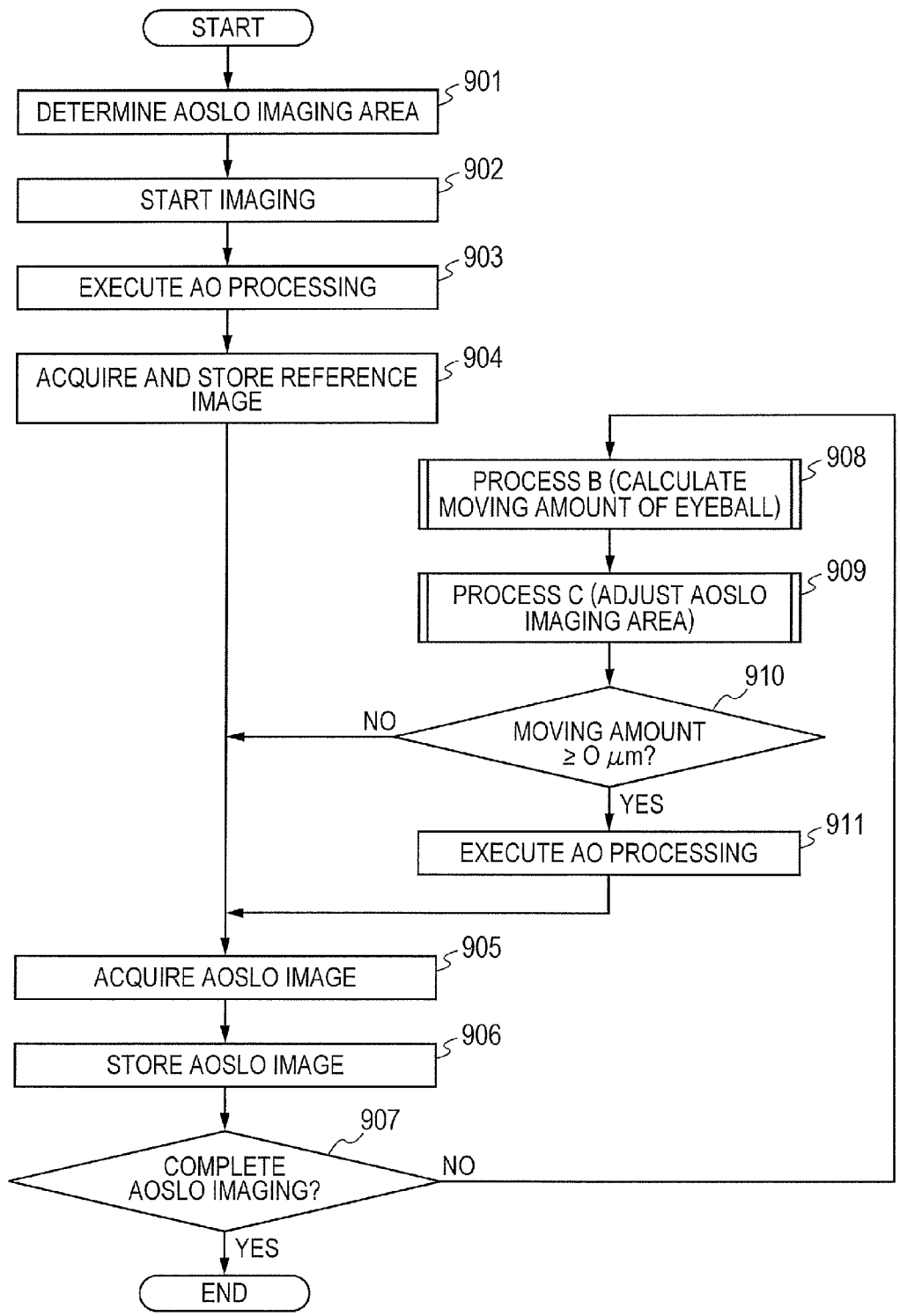
FIG. 9 is a procedure flow schematic diagram in the second embodiment.

With the above-mentioned apparatus, positional information is calculated from an AO-SLO image, and a position change thereof is fed back to the scanners of the AO-SLO apparatus and the wavefront correction device, to thereby acquire the AO-SLO image of a desired position stably. A flow thereof is illustrated in FIG. 9. Note that, unless otherwise noted, the processing is executed by the CPU 201.

First, based on an instruction by an operator from an input device (not shown), an AO-SLO imaging area is determined in the SLO image (Step 901). In practice, a turn-on position of the fixation target 161 is changed to adjust an imaging position.

The imaging is started in Step 902. In this step, the wavefront measurement light irradiates the fundus. In Step 903, a sequential AO process is executed. Specifically, the wavefront correction device is driven based on the signal from the wavefront sensor to correct aberration. In this step, the above-mentioned process is repeated to a certain extent and is continued until an aberration amount is decreased to be an arbitrary threshold value or lower. The state of the aberration correction device may be maintained when the aberration amount is decreased to be a certain threshold value, or the AO process in AO-SLO imaging may be continued.

In Step 904, the AO-SLO image to be a reference is acquired. The acquired image is stored as a reference image. This reference image is wholly used as the template.

The AO-SLO apparatus drives the X-Y scanner 208 so as to scan the imaging area determined in Step 901, and acquires an AO-SLO signal so as to form an image (Step 905). Specifically, the AO-SLO apparatus generates the AO-SLO image as a first image of the eye to be inspected based on return light of AO-SLO light as a first beam. After that, the AO-SLO image is stored in the HDD 202 (Step 906).

In order to further acquire an AO-SLO image, template matching is executed in the acquired AO-SLO image, and coordinates of the template are compared with the matched coordinates to calculate the movement of the eyeball (moving amount and direction) (Process B: Step 908). Further, the detection unit detects the movement by comparing the reference image stored as the template with the newly generated image acquired at this stage, and also includes a unit for detecting the movement of the eye to be inspected by the comparison. The operation in Step 908 as Process B is the same as the operation of Process B in the first embodiment.

In addition, because the AO-SLO image has a small imaging area in general, if the eye moves greatly, the taken image may be out of the imaging area of the reference image. Therefore, the large movement of the eye may be measured by a monitor function or the like for checking a face position or a pupil position. Further, it is possible to detect parallel movement and rotation of the pupil position also by using the wavefront sensor 146. Therefore, it is possible to perform high accuracy position detection by using the measured value of the wavefront sensor together with the fundus image for calculating the position information.

The moving amount calculated here is used to control the imaging area correction of the AO-SLO apparatus. This correction is executed by scan range correction of the scanner as the scanning unit and the aberration correction device (Process C: Step 909). The operation in Step 909 as Process C is the same as the operation of Process C in the first embodiment.

When the moving amount of the fundus is an arbitrary threshold value (o) μm or larger (Step 910), it is considered that an aberration state is greatly changed. Therefore, the process proceeds to Step 911, and the AO process is executed again. The AO process is the same as that in Step 903. However, when the AO process is executed also during the AO-SLO imaging, this step is not necessary. In other words, the arbitrary threshold value (o) μm described here is a threshold value for determining whether or not a good image can be acquired due to a change of aberration when the imaging area is changed. When the moving amount is the threshold value or smaller, it is recognized that the acquired fundus image can be used for diagnosis.

After that, the process proceeds to Step 905, and the AO-SLO imaging is continued.

When the AO-SLO imaging is finished, the processing is finished (Yes in Step 907).

As described above, without using another fundus imaging unit different from the AO-SLO, it is possible to track the imaging position. By using a plurality of devices for imaging position adjustment, high accuracy tracking can be executed also in the high resolution AO-SLO, and an AO-SLO image having high image quality can be acquired.

(Other Embodiments)

Further, the present invention can also be realized by performing the following processing. That is, the processing involves supplying software (program) for realizing the functions of the above-mentioned embodiments to a system or an apparatus via a network or various storage media and causing a computer (or a CPU, an MPU, or the like) of the system or the apparatus to read and execute the program.

Note that, the present invention is not limited to the above-mentioned embodiments and can be variously modified or changed without departing from the present invention. For example, in the above-mentioned embodiments, the case where an object to be measured is an eye has been described, but the present invention can also be applied to objects to be measured such as skin and an organ other than an eye. In this case, the present invention has an embodiment mode as medical equipment such as an endoscope rather than an ophthalmologic apparatus. Thus, it is preferred that the present invention be understood as an inspecting apparatus exemplified by an ophthalmologic apparatus, and the eye to be inspected be understood as an embodiment mode of an object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-086790, filed Apr. 17, 2013, which is hereby incorporated by reference herein in its entirety.

What is claimed is:

1. An imaging method comprising:
   irradiating an imaging area of an object to be inspected with a first light beam which is scanned by a scan unit, and taking a first image of the object to be inspected based on return light of the first light beam;
   measuring aberration generated in the object to be inspected;
   correcting the aberration in accordance with the measured aberration using an aberration correcting unit;
   detecting a moving amount of the object to be inspected;
   adjusting the imaging area by using the scan unit so as to correct the detected moving amount having a first amount; and
   adjusting the imaging area by using the aberration correcting unit so as to correct the detected moving amount having a second amount smaller than the first amount, the scan unit not being used for correcting the detected moving amount having the second amount.

2. An imaging method according to claim 1, wherein the detecting of the moving amount is executed based on the return light of the first light beam.

3. An imaging method according to claim 1, wherein the detecting of the moving amount is executed by irradiating the object to be inspected with a second light beam different from the first light beam, and is executed based on a second image of the object to be inspected generated based on return light of the second light beam.

4. An imaging method according to claim 1, wherein the aberration is measured based on measurement return light from the object to be inspected, the return light being obtained by irradiating the object to be inspected with measurement light for measuring the aberration.

5. An imaging method according to claim 1, further comprising separating the moving amount of the object to be inspected into (1) a variation having a large amplitude and a low frequency, and (2) a variation having a small amplitude and a high frequency,
wherein the imaging area is adjusted by using the scan unit so as to correct the variation having a large amplitude and a low frequency and the imaging area is adjusted by using the aberration correcting unit so as to correct the variation having a small amplitude and a high frequency.

6. An imaging method according to claim 1, wherein the imaging area is adjusted by changing a scan range of the scan unit when the detected moving amount is larger than a predetermined threshold value.

7. An imaging method according to claim 1, wherein a scan range of the scan unit is limited when the detected moving amount is not larger than a predetermined threshold value.

8. A non-transitory tangible medium having recorded thereon a program for causing a computer to perform the imaging method according to claim 1.

9. An imaging apparatus comprising:
an imaging unit configured to irradiate an imaging area of an object to be inspected with a first light beam which is scanned by a scan unit, and to take an image of the object to be inspected based on return light of the first light beam;
an aberration measuring unit configured to measure aberration generated in the object to be inspected;
an aberration correcting unit configured to correct the aberration in accordance with the measured aberration;
a detection unit configured to detect a moving amount of the object to be inspected; and
a control unit configured to adjust the imaging area by using the scan unit so as to correct the detected moving amount having a first amount, and to adjust the imaging area by using the aberration correcting unit so as to correct the detected moving amount having a second amount smaller than the first amount, the scan unit not being used for correcting the detected moving amount having the second amount.

10. An imaging apparatus according to claim 9, further comprising a second light beam irradiation unit configured to irradiate the object to be inspected with a second light beam different from the first light beam,
wherein the detection unit detects the moving amount of the object to be inspected by using an image of the object to be inspected acquired based on return light of the second light beam.

11. An imaging apparatus according to claim 9, further comprising a unit configured to change an irradiation direction of the first light beam,
wherein the moving amount of the object to be inspected is separated in terms of a frequency thereof, and
wherein the unit configured to change the irradiation direction of the first light beam and the aberration correcting unit are controlled based on the separated frequency.

12. An imaging method according to claim 1, wherein the imaging area is adjusted by using the scan unit when the detected moving amount is larger than a predetermined threshold value, and the imaging area is adjusted by using the aberration correcting unit when the detected moving amount is not larger than the predetermined threshold value.

13. An imaging method according to claim 1, wherein the imaging area is adjusted by tracking a movement of the object to be inspected, the tracking being executed by at least one of: (1) using the scan unit, and (2) using the aberration correcting unit.

14. An imaging method according to claim 1, wherein the object to be inspected is an eye.

15. An imaging method according to claim 1, wherein the adjusting the imaging area by using the scan unit is executed by changing an irradiation direction of the first light beam.

16. An imaging method according to claim 1, wherein the adjusting the imaging area by using the aberration correcting unit is executed together with the correcting the aberration.

17. An imaging apparatus according to claim 9, wherein the control unit is configured to adjust the imaging area by using the scan unit when the detected moving amount is larger than a predetermined threshold value, and to adjust the imaging area by using the aberration correcting unit when the detected moving amount is not larger than the predetermined threshold value.

18. An imaging apparatus according to claim 9, wherein the control unit is configured to adjust the imaging area by using the aberration correcting unit together with correcting the aberration by the aberration correcting unit.

* * * * *